US011485757B2

(12) United States Patent
Ichimura

(10) Patent No.: US 11,485,757 B2
(45) Date of Patent: Nov. 1, 2022

(54) OLIGOPEPTIDE SEARCH METHOD, OLIGOPEPTIDE, MODIFIED PEPTIDE, AND IMMUNOASSAY METHOD

(71) Applicant: ZEON CORPORATION, Tokyo (JP)

(72) Inventor: Naoya Ichimura, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 276 days.

(21) Appl. No.: 16/467,171

(22) PCT Filed: Dec. 21, 2017

(86) PCT No.: PCT/JP2017/046019
§ 371 (c)(1),
(2) Date: Jun. 6, 2019

(87) PCT Pub. No.: WO2018/117242
PCT Pub. Date: Jun. 28, 2018

(65) Prior Publication Data
US 2019/0331671 A1    Oct. 31, 2019

(30) Foreign Application Priority Data
Dec. 22, 2016   (JP) .............................. JP2016-248711

(51) Int. Cl.
*G01N 33/545*   (2006.01)
*C07K 7/06*     (2006.01)
*G01N 33/543*   (2006.01)

(52) U.S. Cl.
CPC ............ *C07K 7/06* (2013.01); *G01N 33/545* (2013.01); *G01N 33/54353* (2013.01)

(58) Field of Classification Search
CPC .... C07K 7/06; C40B 30/10; G01N 33/54353; G01N 33/545; G01N 33/548; G01N 33/6818
See application file for complete search history.

(56) References Cited

U.S. PATENT DOCUMENTS

| 7,253,142 B1 | 8/2007 | Suzuki et al. |
| 8,697,655 B2 | 4/2014 | Wada et al. |
| 2013/0045917 A1 | 2/2013 | Wada et al. |
| 2013/0316932 A1 | 11/2013 | Nishimura et al. |
| 2017/0130203 A1 | 5/2017 | Ichimura et al. |

FOREIGN PATENT DOCUMENTS

| JP | 2006275769 A | 10/2006 |
| JP | 2007240461 A | 9/2007 |
| JP | 2009080119 A | 4/2009 |
| JP | 2009136280 A | 6/2009 |
| JP | 2010117189 A | 5/2010 |
| JP | 2011168610 A | 9/2011 |
| JP | 5863045 B2 | 2/2016 |
| JP | 2016038265 A | 3/2016 |
| WO | 2011111832 A1 | 9/2011 |
| WO | 2012070564 A1 | 5/2012 |
| WO | 2015199119 A1 | 12/2015 |

OTHER PUBLICATIONS

Jirimutu. et al. Genome sequences of wild and domestic bactrian camels. Nat. Commun. 3:1202 doi: 10.1038/ncomms2192 (2012) (Year: 2012).*
Sep. 17, 2020, the Extended European Search Report issued by the European Patent Office in the corresponding European Patent Application No. 17882686.3.
Jun. 17, 2020, the Partial Supplementary European Search Report issued by the European Patent Office in the corresponding European Patent Application No. 17882686.3.
Takaaki Date et al., Polymer-Binding Peptides for the Noncovalent Modification of Polymer Surfaces: Effects of Peptide Density on the Subsequent Immobilization of Functional Proteins, ACS Applied Materials and Interfaces, 2011, pp. 351-359, vol. 3.
Urartu Ozgur Safak Seker et al., Material Binding Peptides for Nanotechnology, Molecules, 2011, pp. 1426-1451, vol. 16.
Mar. 20, 2018, International Search Report issued in the International Patent Application No. PCT/JP2017/046019.
Jun. 25, 2019, International Preliminary Report on Patentability issued in the International Patent Application No. PCT/JP2017/046019.
Oct. 8, 2021, the Extended European Search Report issued by the European Patent Office in the corresponding European Patent Application No. 21166354.7.
Anonymous, "RecName: Full=LEH domain-containing protein {ECO:0000259|Pfam:PF07858};", Database Uniprot [Online], Dec. 9, 2015, XP055845938, retrieved from EBI accession No. Uniprot: AOAONOYFT5, Database accession No. AOAONOYFT5.

\* cited by examiner

*Primary Examiner* — Galina M. Yakovleva
(74) *Attorney, Agent, or Firm* — Kenja IP Law PC

(57) ABSTRACT

Provided is a method for efficiently searching a peptide library for an oligopeptide that can be bound to the end of a protein or peptide of interest. Further, provided is an efficient and highly safe immunoassay.

3 Claims, 9 Drawing Sheets

Specification includes a Sequence Listing.

SEQUENCE LISTING

<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

```
Thr Val Asp Ser Cys Leu Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Thr Val Asp Asn Ser Leu Ala
1               5

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Ala Tyr Thr Val Asp Asn Ser Leu Ala Cys
1               5                   10

Gly Gly Gly Gly Gly His His His His His
                15                  20

His

<210> SEQ ID NO 4
<211> LENGTH: 21
<212> TYPE: PRT
<213> ORGANISM: Artificial Sequence
<220> FEATURE:
<223> OTHER INFORMATION: Synthetic

<400> SEQUENCE: 4

Ala Cys Thr Val Asp Ser Cys Leu Thr Cys
1               5                   10

Gly Gly Gly Gly Gly His His His His His
                15                  20

His

<210> SEQ ID NO 5
<211> LENGTH: 26
<212> TYPE: PRT
<213> ORGANISM: Artificial Sequence
<220> FEATURE:
<223> OTHER INFORMATION: Synthetic

<400> SEQUENCE: 5

Ala Cys Thr Val Asp Ser Cys Leu Thr Cys
1               5                   10

Gly Gly Gly Gly Gly Arg Gly Asp Ser Pro
                15                  20

His His His His His His
                25

<210> SEQ ID NO 6
<211> LENGTH: 7
<212> TYPE: PRT
<213> ORGANISM: Artificial Sequence
<220> FEATURE:
<223> OTHER INFORMATION: Synthetic
```

```
<400> SEQUENCE: 6

Cys Lys Val Leu Arg Arg His
1               5

<210> SEQ ID NO 7
<211> LENGTH: 21
<212> TYPE: PRT
<213> ORGANISM: Artificial Sequence
<220> FEATURE:
<223> OTHER INFORMATION: Synthetic

<400> SEQUENCE: 7

Ala Cys Thr Val Asp Ser Cys Leu Thr Cys
1               5                   10

Gly Gly Gly Gly Gly Ser Ser Ser Gly Leu
                15                  20

Gly
```

OLIGOPEPTIDE SEARCH METHOD, OLIGOPEPTIDE, MODIFIED PEPTIDE, AND IMMUNOASSAY METHOD

TECHNICAL FIELD

The disclosure relates to an oligopeptide search method as well as an oligopeptide having a specific amino acid sequence, a modified peptide, and an immunoassay method.

BACKGROUND

It is known that the proliferation property of a recombinant cell and the expression amount of a recombinant gene are improved by using a molded product made of a norbornene-based polymer as a culture container (Patent Literature 1).

In addition, it is known that a molded product made of a norbornene-based polymer is suitable for long-term storage of a protein solution formulation because it hardly causes aggregation, denaturation, and degradation of proteins (Patent Literature 2, etc.).

In addition, as a method for detecting and quantifying a trace substance, an antigen-antibody reaction method generally called ELISA (Enzyme Linked Immuno Sorbent Assay) is widely used. Generally, in an ELISA, a reaction between a protein such as an antibody or an antigen immobilized on an inner surface of a container such as a plastic microwell plate and a test substance in a specimen is detected directly or indirectly.

By the way, in recent years, technologies have been developed in which physiologically active substances such as peptides and the like are immobilized on substrates, whereby parallel detection, analysis, and the like of target substances in biological samples are performed.

It has been proposed that a surface of a substrate for immobilizing a physiologically active substance used for such a detection, analysis, and the like, such as a substrate made of a norbornene-based polymer is coated with a polymer compound composed of a unit having a phosphorylcholine group, a unit having a hydrophobic group, and a unit having an aldehyde group or a maleimide group in order to suppress non-specific adsorption/binding of a substance to be detected and immobilize the physiologically active substance (Patent Literature 3).

CITATION LIST

Patent Literature

PTL 1: WO2015/199119
PTL 2: Unexamined Japanese Patent Application Kokai Publication No. 2011-168610
PTL 3: Unexamined Japanese Patent Application Kokai Publication No. 2010-117189
PTL 4: Unexamined Japanese Patent Application Kokai Publication No. 2009-080119

SUMMARY

Technical Problem

However, in a method of Patent Literature 3, since a surface of a molded product in contact with a protein is coated with a polymer compound other than a norbornene-based polymer, there is a problem that the protein stabilization effect of the norbornene-based polymer is reduced.

In addition, since a molded product composed of a norbornene-based polymer is known to have low fluorescence (Patent Literature 4), it is considered to be suitable for an ELISA in which fluorescence detection is generally used. However, since the physical adsorptivity of a substance such as a protein to the material surface of a norbornene-based polymer is weaker than to the material surface of polystyrene, there is a problem that it is difficult to immobilize an antibody or an antigen on the surface.

In addition, in an ELISA, although an operation to remove a measurement sample from a well and an operation to wash the well are required after the measurement sample is added to the well, the measurement sample may be contaminated with a virus or a microorganism that causes infection. Therefore, as an additional problem, there is an infection risk due to the possibility of receiving liquid droplets during the measurement operations.

The disclosure has been made in view of the circumstances of the prior art, and an object thereof is to provide a method for efficiently searching a peptide library for an oligopeptide that can be bound to the end of a target protein or peptide. Another object is to provide an efficient and highly safe immunoassay.

Solution to Problem

The inventors have conceived that by using an oligopeptide that can be bound to the end of a target protein or peptide and has adhesiveness to a norbornene-based polymer, the target protein or peptide can be efficiently immobilized directly on the norbornene-based polymer without reducing the protein stabilization effect of the norbornene-based polymer, and conducted intensive studies to solve the problems set forth above.

As a result, the inventors discovered that when a peptide library is exposed to a molded product made of a norbornene-based polymer and then washed with an aqueous solvent, a peptide having high adhesiveness to the norbornene-based polymer can be obtained on the surface of the molded product. In this manner, the inventors completed the present disclosure.

Thus, according to the present disclosure, the following oligopeptide search methods (1) to (4), oligopeptides (5) to (7), a modified peptide or modified polypeptide (8), and immunoassay methods (9) to (12) are provided.

(1) An oligopeptide search method comprising the steps of:
  (I) exposing a peptide library containing a random amino acid sequence to the surface of a molded product at least the surface of which is composed of a norbornene-based polymer;
  (II) washing the exposed surface with an aqueous solvent;
  (III) recovering the compound remaining on the surface by washing the surface with an organic solvent; and
  (IV) analyzing the peptide sequence information of the recovered compound.

(2) The oligopeptide search method according to (1), wherein the norbornene-based polymer is a hydrogenated ring-opened polymer of a norbornene-based monomer.

(3) The oligopeptide search method according to (1) or (2), wherein the aqueous solvent is a buffer.

(4) The oligopeptide search method according to any one of (1) to (3), wherein the organic solvent is a polar organic solvent.

(5) An oligopeptide having the amino acid sequence of Thr-Val-Asp-Ser-Cys-Leu-Thr (SEQ ID NO: 1).

(6) The oligopeptide according to (5), whierein the oligopeptide has adhesiveness to a norbornene-based polymer.

(7) The oligopeptide according to (6), wherein the norbornene-based polymer is a hydrogenated ring-opened polymer of a norbornene-based monomer.
(8) A modified peptide or a modified polypeptide having the amino acid sequence of Thr-Val-Asp-Ser-Cys-Leu-Thr (SEQ ID NO: 1) and having adhesiveness to a norbornene-based polymer.
(9) An immunoassay method comprising immobilizing the oligopeptide searched by the search method according to any one of (1) to (4) on the inner surface of a container composed of a norbornene-based polymer, and
performing a measurement using the container having the inner surface on which the oligopeptide is immobilized.
(10) The immunoassay method according to (9), wherein the norbornene-based polymer is a hydrogenated ring-opened polymer of a norbornene-based monomer.
(11) The immunoassay method according to (9) or (10), wherein the oligopeptide has the amino acid sequence of Thr-Val-Asp-Ser-Cys-Leu-Thr (SEQ ID NO: 1).
(12) The immunoassay method according to any one of (9) to (11), further comprising blocking before the measurement,
wherein Tween® 20 is used as a blocking agent.

Advantageous Effect

According to the present disclosure, it is possible to provide a method for efficiently searching a peptide library for an oligopeptide that can be bound to the end of a target protein or peptide. In addition, according to the present disclosure, it is possible to provide an efficient and highly safe immunoassay.

BRIEF DESCRIPTION OF THE DRAWINGS

In the accompanying drawings.

DETAILED DESCRIPTION

Figure 1:
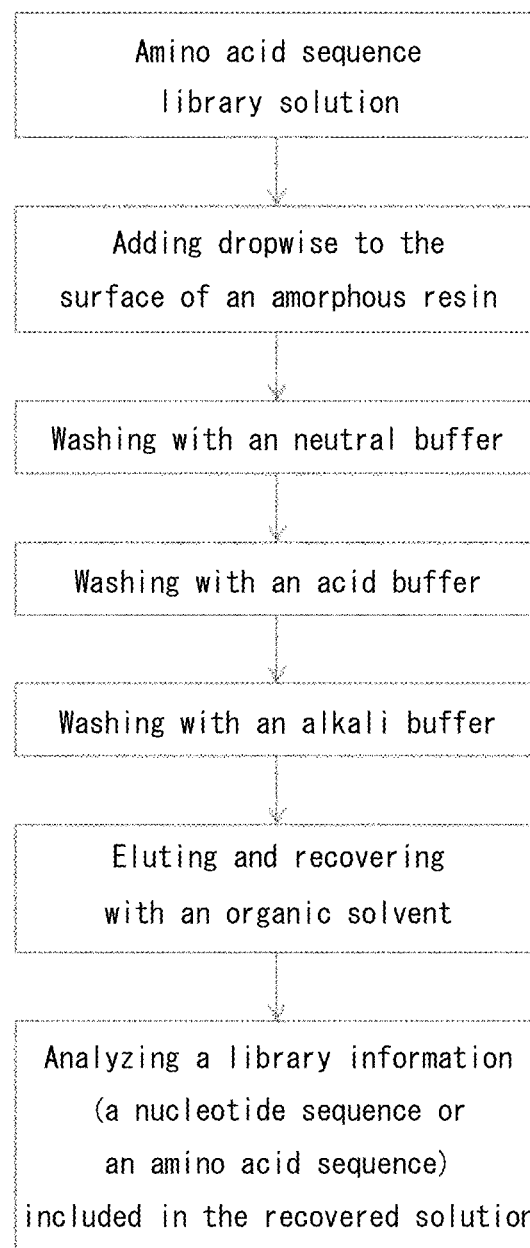
FIG. 1 is a figure depicting a procedure of a method for searching an oligopeptide having adhesiveness to a norbornene-based polymer, according to one of the disclosed embodiments.

Hereinafter, detailed descriptions of the embodiments of the present disclosure will be given while being divided into 1) oligopeptide search method, 2) oligopeptide, and 3) modified peptide or modified polypeptide having adhesiveness to a norbornene-based polymer, and 4) immunoassay method.

1) Oligopeptide Search Method

The first aspect is an oligopeptide search method comprising the steps of: (I) exposing a peptide library containing a random amino acid sequence to the surface of a molded product at least the surface of which is composed of a norbornene-based polymer; (II) washing the exposed surface with an aqueous solvent; (III) recovering the compound remaining on the surface by washing the surface with an organic solvent; and (IV) analyzing the peptide sequence information of the recovered compound.

<Step (I)>

Step (1) is a step of exposing a peptide library containing a random amino acid sequence to the surface of a molded product at least the surface of which is composed of a norbornene-based polymer.

The peptide library used in the above-mentioned search method is one containing a random amino acid sequence, including one in general use as a peptide library. Examples of the peptide library may include a peptide mixture of peptides obtainable by organic synthesis with random amino acid sequences, peptides obtainable by random cleavage of proteins, or the like; and a display library in which a protein having a random amino acid sequence at the terminal region is displayed on the surface of a virus particle such as a phage.

In the search method according to one of the disclosed aspects, a molded product at least the surface of which is composed of a norbornene-based polymer is used. That is, in the above-mentioned molded product, a molded product surface which is exposed to a peptide library may be composed of at least a norbornene-based polymer. In addition, the molded product surface may be composed of only a norbornene-based polymer, or the whole of the molded product may be composed of only a norbornene-based polymer.

The norbornene-based polymer is a polymer containing a monomer unit having a norbornene skeleton in an amount of 50 mass % or more, preferably 60 mass % or more, based on all the monomer units constituting the norbornene-based polymer. More specifically, the norbornene-based polymer is obtainable by polymerizing a norbornene-based monomer which is a monomer having a norbornene skeleton, and roughly divided into one obtainable by ring-opening polymerization and one obtainable by addition polymerization.

Examples of the one obtainable by ring-opening polymerization include a ring-opened polymer of a norbornene-based monomer, a ring-opened polymer of a norbornene-based monomer and other monomer capable of ring-opening copolymerization therewith, and a hydride thereof.

Examples of the one obtainable by addition polymerization include an addition polymer of a norbornene-based monomer, and an addition polymer of a norbornene-based monomer and other monomer copolymerizable therewith.

The norbornene-based polymers may be used individually or two or more norbornene-based polymers may be used in combination.

Among these, a hydrogenated ring-opened polymer of a norbornene-based monomer is preferable because the effect of what is disclosed is more easily obtainable.

Examples of the norbornene-based monomer usable for the synthesis of the norbornene-based polymer include bicyclic monomers such as bicyclo[2.2.1]hept-2-ene (common name: norbornene), 5-methyl-bicyclo[2.2.1]hept-2-ene, 5,5-dimethyl-bicyclo[2.2.1]hept-2-ene, 5-ethyl-bicyclo[2.2.1]hept-2-ene, 5-ethylidene-bicyclo[2.2.1]hept-2-ene, 5-vinyl-bicyclo[2.2.1]hept-2-en, 5-propenylbicyclo[2.2.1]hept-2-ene, 5-methoxycarbonyl-bicyclo[2.2.1]hept-2-ene, 5-cyanobicyclo[2.2.1]hept-2-en, and 5-methyl-5-methoxycarbonyl-bicyclo[2.2.1]hept-2-ene;

tricyclic monomers such as tricyclo[4.3.0$^{1,6}$.1$^{2,5}$]dec-3,7-diene (common name: dicyclopentadiene), 2-methyldicyclopentadiene, 2,3-dimethyldicyclopentadiene, and 2,3-dihydroxydicyclopentadiene; and tetracyclic monomers such as tetracyclo[4.4.0.1$^{2,5}$.1$^{7,10}$]-3-dodecene (tetracyclododecene), tetracyclo[4.4.0.1$^{2,5}$.1$^{7,10}$]-3-dodecene, 8-methyltetracyclo[4.4.0.1$^{2,5}$.1$^{7,10}$]-3-dodecene, 8-ethyltetracyclo[4.4.0.1$^{2,5}$.1$^{7,10}$]-3-dodecene, 8-ethylidenetetracyclo[4.4.0.1$^{2,5}$.1$^{7,10}$]-3-dodecene, 8,9-dimethyltetracyclo[4.4.0.1$^{2,5}$.1$^{7,10}$]-3-dodecene, 8-ethyl-9-metyltetracyclo[4.4.0.1$^{2,5}$.1$^{7,10}$]-3-dodecene, 8-ethylidene-9-methyltetracyclo[4.4.0.1$^{2,5}$.1$^{7,10}$]-3-dodecene, 8-methyl-8-carboxymethyltetracyclo[4.4.0.1$^{2,5}$.1$^{7,10}$]-3-dodecene, 7,8-benzotricyclo[4.3.0.1$^{2,5}$]dec-3-en (common name: methanotetrahydrofluorene: also referred to as 1,4-methano-1,4,4a,9a-tetrahydrofluorene), 1,4-methano-8-methyl-1,4,4a,9a-tetrahydrofluorene, 1,4-methano-8-chloro-1,4,4a,9a-tetrahydrofluorene, and 1,4-methano-8-bromo-1,4,4a,9a-tetrahydrofluorene.

These norbornene monomers may have one or more kinds of substituents. Examples of the substituents include alkyl, alkylene, aryl, silyl, alkoxycarbonyl, and alkylidene groups.

Examples of the other monomer capable of ring-opening copolymerization with a norbornene-based monomer include monocyclic cycloolefin monomers such as cyclohexene, cycloheptene, cyclooctene, 1,4-cyclohexadiene, 1,5-cyclooctadiene, 1,5-cyclodecadiene, 1,5,9-cyclododecatriene, and 1,5,9,13-cyclohexadecatetraene.

Examples of the other monomer capable of addition copolymerization with a norbornene-based monomer include $C_2$-$C_{20}$ α-olefin-based monomers such as ethylene, propylene, 1-butene, 1-pentene, and 1-hexene; cycloolefin-based monomers such as cyclobutene, cyclopentene, cyclohexene, cyclooctene, and tetracyclo[9.2.1.0$^{2,10}$.0$^{3,8}$]tetradec-3,5,7,12-tetraene (also referred to as 3a,5,6,7a-tetrahydro-4,7-methano-1H-indene); and non-conjugated diene-based monomers such as 1,4-hexadiene, 4-methyl-1,4-hexadiene, 5-methyl-1,4-hexadiene, and 1,7-octadiene.

Among these, as the other monomer capable of addition copolymerization with a norbornene-based monomer, α-olefin-based monomer is preferable, and ethylene is more preferable.

These other monomers may have one or more kinds of substituents. Examples of the substituents include alkyl, alkylene, aryl, silyl, alkoxycarbonyl, and alkylidene groups.

The ring-opened polymer of a norbornene-based monomer, or the ring-opened polymer of a norbornene-based monomer and other monomer capable of ring-opening copolymerization therewith can be obtained by polymerizing monomer components in the presence of a known catalyst for ring-opening polymerization.

As the catalyst for ring-opening polymerization, for example, a catalyst consisting of a halide, a nitrate, or an acetylacetone compound of a metal such as ruthenium or osmium and a reductant, or a catalyst consisting of a halide or an acetylacetone compound of a metal such as titanium, zirconium, tungsten, or molybdenum and an organic aluminum compound can be used.

The hydrogenated ring-opened polymer of a norbornene-based polymer can be usually obtained by adding a known hydrogenation catalyst containing a transition metal such as nickel or palladium to the polymerization solution of the above-mentioned ring-opened polymer to hydrogenate a carbon-carbon unsaturated bond.

The addition polymer of a norbornene-based monomer, or the addition polymer of a norbornene-based monomer and other monomer copolymerizable therewith can be obtained by polymerizing monomer components in the presence of a known catalyst for addition polymerization.

As the catalyst for addition polymerization, for example, a catalyst consisting of a titanium, zirconium or vanadium compound and an organoaluminum compound can be used.

The molecular weight of the norbornene-based polymer is not restricted and the weight-average molecular weight in terms of polystyrene measured by gel permeation chromatography (GPC) of a cyclohexane solution (a toluene solution when the polymer is not dissolved) is usually 5,000 or more, preferably 5,000 to 500,000, more preferably 8,000 to 200,000, and particularly preferably 10,000 to 100,000. When the weight-average molecular weight is within this range, mechanical strength and processability are highly balanced and suitable.

The glass transition temperature of the norbornene-based polymer may be selected as appropriate according to the purpose of use and it is usually 50 to 300° C., preferably 100 to 280° C., particularly preferably 115 to 250° C., and more preferably 130 to 200° C. When the glass-transition temperature is within this range, heat resistance and processability are highly balanced and suitable.

The glass-transition temperature of the norbornene-based polymer set forth above was measured according to JIS K 7121.

The norbornene-based polymers may be used individually or two or more norbornene-based polymers may be used in combination.

Further, as a resin component that constitutes the surface of the molded product, in addition to the norbornene-based polymer, optionally, a compounding agent used usually in a thermoplastic resin material such as a soft polymer, an antioxidant, an ultraviolet absorber, a light stabilizer, a near-infrared absorber, a mold release agent, a coloring agent such as a dye or a pigment, a plasticizer, an antistatic agent, or a fluorescent brightening agent can be added in an amount adopted normally. Here, when a soft polymer is used and mixed with the norbornene-based polymer, the amount is usually 0.01 to 20 parts by mass, preferably 0.05 to 10 parts by mass, and more preferably 0.05 to 5 parts by mass, based on 100 parts by mass of an alicyclic structure-containing polymer which is a norbornene-based polymer.

In addition, as a resin component constituting the surface of the molded product, a polymer other than the norbornene-based polymer and the soft polymer which is one of the above-mentioned compounding agents (hereinafter simply referred to as an "other polymer") may be mixed. The amount of the other polymer mixed with the norbornene-based polymer is usually 200 parts by mass or less, preferably 150 parts by mass or less, and more preferably 100 parts by mass or less, based on 100 parts by mass of the norbornene-based polymer.

If the proportions of various compounding agents and other polymers to be mixed to the norbornene-based polymer are too large, it becomes difficult for cells to float. Therefore it is preferable that any of them is mixed within a range in which the properties of the alicyclic structure-containing polymer are not impaired.

No specific limitations are placed on the method of mixing the norbornene-based polymer with the compounding agent or the other polymer so long as the compounding agent is sufficiently dispersed in the polymer. The order of mixing is also not limited. Examples of the compounding method include a method in which a resin is kneaded in a molten state using a mixer, a single-screw kneader, a twin-screw kneader, a roll, a brabender, an extruder, or the like; and a method in which a resin is dissolved and dispersed in a suitable solvent, followed by removing the solvent by a coagulation method, a casting method, or a direct drying method.

When a twin-screw kneader is used, after kneading, the resin is often extruded usually in a molten state into a rod, cut into an appropriate length with a strand cutter, and pelletized for use.

Using such a norbornene-based polymer, usually, a molded product having an arbitrary shape can be obtained by any molding method, for example, an injection molding method, an extrusion molding method, a blow molding method, a vacuum molding method, a press molding method, a compression molding method, a rotational molding method, a cast molding method, or the like.

Examples of the molded product composed of a norbornene-based polymer (norbornene-based polymer molded product) include a culture vessel made of a norbornene-based polymer in the case of using the norbornene-based polymer molded product for cell culture.

For example, if the norbornene-based polymer molded product is a dish-like culture vessel, it can be molded by an injection molding method or the like.

Note that in the above-mentioned culture vessel, a surface of a portion to which a peptide library is exposed may be composed of at least a norbornene-based polymer.

In addition, the surface of a portion to which a peptide library is exposed may be composed of only a norbornene-based polymer, or the whole of the culture vessel may be composed of only a norbornene-based polymer.

It is preferable to use the molded product obtained by molding in the peptide search method according to one of the aspects without a hydrophilic treatment by a plasma irradiation or the like. This is because the surface is oxidized by a hydrophilic treatment, whereby a peptide adheres non-specifically to the oxidized surface, so the number of kinds of peptides remaining on the surface increases, resulting in a risk of making it difficult to search for a specific peptide.

The above-mentioned norbornene-based polymer molded product is usually used after sterilization.

The method of sterilization is not restricted and can be appropriately selected from methods generally adopted in the medical field depending on the shape of the molded product and a cell used such as heating methods including a high pressure steam method and a dry heat method; a radiation method of irradiating a radiation such as a γ ray or an electron beam and a irradiation method of irradiating a high frequency; a gas method of contacting with a gas such as ethylene oxide gas (EOG); and a filtration method using a sterilizing filter.

By bringing the surface of the molded norbornene-based polymer molded product (the inner surface of the culture vessel made of a norbornene-based polymer) into contact with an oligopeptide or a modified (poly)peptide having adhesiveness to a norbornene-based polymer according to one of the aspects, the oligopeptide or the modified (poly)peptide having adhesiveness to a norbornene-based polymer can be attached to the surface of the molded product (the inner surface of the culture vessel).

In the step of exposing a peptide library having a random amino acid sequence to the surface of a molded product at least the surface of which is composed of a norbornene-based polymer, for example, a method is employed in which a peptide library solution in which a peptide library is dissolved or suspended in a substantially neutral liquid medium such as a phosphate buffer or a cell culture solution that does not cause denaturation of the peptide library is brought into contact with the above-described surface. The contact time is usually 1 minute to 10 hours, and preferably 5 minutes to 2 hours. In a case in which the contact time is too short, there is a risk that an adhesive peptide does not sufficiently adhere to the molded product, and conversely in a case in which the contact time is too long, there is a risk that a peptide which originally does not have adhesiveness to the molded product adheres due to denaturation, etc. of the peptide. Therefore, neither of the cases is preferable. The temperature at contact is usually 15 to 35° C., and preferably 20 to 30° C. In a case in which the temperature is too high, evaporation of the peptide library solution may proceed, while in a case in which the temperature is too low, the original adhesiveness of the peptide library may not be obtained. Therefore, neither of the cases is preferable.

<Step (II)>

Step (II) is a step of washing the exposed surface with an aqueous solvent after the exposure of step (I).

The aqueous solvent to be used is preferably a combination of three kinds, i.e., a buffer, an acidic aqueous solution, and a basic aqueous solution, because it is easy to select one having a specific adhesiveness to a norbornene-based polymer. The order of washing with the aqueous solvent can be set arbitrarily. Among these, a buffer is preferable because the effect of what is disclosed is more easily obtainable.

The buffer is a solution in which the pH does not change significantly even if a small amount of an acid or a base is added or the concentration changes slightly.

As the buffer, one having a pH of 5 to 9, preferably a pH of 6.8 to 8.3 is usually used. Specific examples of the buffer include, but are not limited to, a phosphate buffer containing phosphoric acid as a buffer component, a phosphate buffered saline obtained by adding sodium chloride to a phosphate buffer, an acetate buffer containing acetic acid as a buffer component, a citrate buffer containing citric acid as a buffer component, a boric acid buffer containing boric acid as a buffer component, a tris buffer containing trishydroxymethylaminomethane as a buffer component, and a buffer solution obtained by adding a metal chelating agent such as EDTA or boric acid or acetic acid to a Tris buffer.

These buffers may be used individually or two or more of them may be used in combination.

As the acidic aqueous solution, one having a pH of 1 to 4, preferably a pH of 2.5 to 3 is usually used. Examples of the acid used for preparation of the acidic aqueous solution include hydrochloric acid, sulfuric acid, phosphoric acid, trifluoroacetic acid, an aqueous glycine solution in which the pH is adjusted with an acid, and an aqueous citric acid solution in which the pH is adjusted with an acid.

Among these, a diluted acid solution having a concentration of a few mM, a glycine solution having a pH adjusted to about 2.5 which can be easily adjusted to a neutral pH by mixing about 1 M aqueous trishydroxymethylaminomethane solution, and the like are preferable in view of an operation to quickly bring the pH to a neutral condition after recovery of the peptide library exposed to the pH of the acidic aqueous solution.

These acidic aqueous solutions may be used individually or two or more of them may be used in combination.

As the basic aqueous solution, one having a pH of 8 to 11.5, preferably a pH of 10 to 11.5 is usually used. Examples of the base used for preparation of the basic aqueous solution include an aqueous amine such as triethylamine or triethanolamine, ammonia, an ammonium salt such as ammonium hydroxide, sodium hydroxide, potassium hydroxide, calcium hydroxide, and an aqueous solution of glycine in which the pH is adjusted with sodium hydroxide.

Among these, an ammonia salt aqueous solution or an aqueous solution of glycine which has been brought to a dilute concentration of 200 mM or less by the above-mentioned basic aqueous solution is preferable in view of an operation to quickly bring the pH to a neutral condition after recovery of the peptide library exposed to the pH of the basic aqueous solution. These basic aqueous solutions may be used individually or two or more of them may be used in combination.

The number of times of washing with the aqueous solvent and the amount of the aqueous solvent used for washing can be arbitrarily selected depending on the shape and the area of the part to be washed. In the case of a flat surface such as a conventional culture dish, the number of times of washing with each of the buffer, the acidic aqueous solution, and the basic aqueous solution is usually 1 to 5, and preferably 2 to 4. The amount of the aqueous solvent used for one washing is usually 10 to 0.01 ml/cm$^2$, and preferably 2 to 0.1 ml/cm$^2$ per area to be washed. If the amount of the aqueous solvent is too small, washing becomes insufficient, while if the aqueous solvent is used in a large amount, it becomes wasted because the washing effect is limited.

<Step (III)>

Step (III) is a step of recovering the compound remaining on the molded product surface by washing the molded product surface with an organic solvent.

After washing with the aqueous solvent in step (II), washing is carried out with an organic solvent in order to recover the compound remaining on the surface of the norbornene-based polymer molded product.

It is considered that the peptide which endures washing with the aqueous solvent and remains on the surface of the norbornene-based polymer molded product has high adhesiveness to the norbornene-based polymer.

Although the organic solvent used for washing can also be used without dilution in an aqueous medium, in the case of a screening system utilizing virus growth characteristics such as a display library, the organic solvent is preferably used as a diluted solution diluted in an aqueous medium because the influence on the growth characteristics can be reduced. Therefore, the organic solvent used in the disclosure is preferably a polar organic solvent miscible with water.

Examples of the polar organic solvent include a sulfur-containing organic solvent such as dimethylsulfoxide; an amide organic solvent such as dimethylformamide; alcohol organic solvents such as methanol and isopropanol; and a nitrile organic solvent such as acetonitrile.

The concentration of the polar solvent in the case of being diluted with an aqueous medium is usually 5% by weight to 90% by weight, and preferably 5% by weight to 50% by weight, based on the total weight of the diluted solution.

The number of times of washing with the organic solvent and the amount of the organic solvent used for washing can be arbitrarily selected depending on the shape and the area of the part to be washed. In a case in which the molded product surface is a flat surface such as a conventional culture dish, the number of times of washing with the organic solvent is usually 1 to 5, and preferably 1 to 2.

The amount of the organic solvent (the diluted solution thereof in a case in which it has been diluted with an aqueous medium) used for one washing is usually 0.01 to 10 ml/cm$^2$, and preferably 0.1 to 2 ml/cm$^2$.

If the amount of the organic solvent used for washing is too small, washing becomes insufficient, while if the organic solvent is used in a large amount, it becomes wasted because the washing effect is limited.

<Step (IV)>

Step (IV) is a step of analyzing the peptide sequence information of the compound recovered in step (III).

That is, the peptide sequence information in the solution that is collected after washing treatment with an organic solvent is analyzed to confirm the amino acid sequence of the polyoligopeptide having adhesiveness to a norbornene-based polymer.

In the case of using a display library including a peptide mixture and a polymer particle in which a protein having a random amino acid sequence at a partial region (usually a terminal region) is displayed as a peptide library, the amino acid sequence can be directly confirmed by a known amino acid sequence analysis (mass analysis, etc.).

In addition, when a display library is used, the gene of a phage can be analyzed to determine the corresponding amino acid sequence.

2) Oligopeptide

The second aspect is an oligopeptide consisting of a specific amino acid sequence. The oligopeptide is a peptide consisting of a relatively small number such as 2 to 10 of amino acids. Examples of the oligopeptide include a polypeptide chain obtainable by enzymatically or chemically degrading a protein (polypeptide).

The oligopeptide according to one of the aspects has the amino acid sequence of Thr-Val-Asp-Ser-Cys-Leu-Thr (hereinafter also referred to as the "specific amino acid sequence"). The oligopeptide having such an amino acid sequence is an oligopeptide having adhesiveness to a norbornene-based polymer. Note that the oligopeptide may consist only of the amino acid sequence of Thr-Val-Asp-Ser-Cys-Leu-Thr (SEQ ID NO: 1).

The oligopeptide according to the second aspect is a kind of oligopeptide which can be searched by the method for searching for a peptide having adhesiveness to a norbornene-based polymer according to the first aspect of the disclosure described above.

3) Modified Peptide or Modified Polypeptide Having Adhesiveness to a Norbornene-Based Polymer The modified peptide or modified polypeptide having adhesiveness to a norbornene-based polymer according to the third aspect (hereinafter referred to as the "norbornene-based polymer-adhesive modified (poly)peptide") has the above-mentioned specific amino acid sequence at the terminus or inside thereof. The norbornene-based polymer-adhesive modified (poly)peptide may be linear or branched.

The norbornene-based polymer-adhesive modified (poly) peptide according to the third aspect can be obtained by addition or insertion of an optional (poly)peptide to the oligopeptide according to the second aspect or substitution of an optional (poly)peptide for a part of amino acids of the oligopeptide.

Examples of the optional (poly)peptide include extracellular matrixes such as laminin, fibronectin, collagen, and vitronectin; cytokines such as interleukin, platelet derived growth factor, hepatocyte growth factor, nerve growth factor, tumor necrosis factor, epidermal growth factor, fibroblast growth factor, transforming growth factor, and adiponectin; (poly) peptides having physiological activity such as cell membrane receptors including integrin and PD-1, and cell surface antigens including CD2 and CD60 as well as antibodies capable of recognizing hapten antigens and protein antigens; and (poly)peptides having useful functions in genetic engineering such as histidine tag, thioredoxin tag, glutathione S-transferase tag, maltose binding protein tag, and fluorescently labeled proteins including GFP and luciferase.

In addition, a linker sequence can be inserted for the purpose of linking the oligopeptide according to the second aspect with the optional (poly)peptide, adjusting the peptide length, or the like.

The norbornene-based polymer-adhesive modified (poly) peptide according to the third aspect contains one or more of the specific amino acid sequences.

"The total number of amino acids constituting the norbornene-based polymer-adhesive modified (poly)peptide according to the third aspect/the number of oligopeptides according to the second aspect contained in the norbornene-based polymer-adhesive modified (poly)peptide according to the third aspect" ($\alpha$) of the norbornene-based polymer-adhesive modified (poly)peptide according to the third aspect is preferably 7 or more and 80 or less, and more preferably 10 or more and 50 or less.

When the $\alpha$ is more than 80, it is preferable that in the oligopeptide according to the second aspect, at least one of the specific amino acid sequence is present within preferably 20, more preferably 10 amino acids from the end of the norbornene-based polymer-adhesive modified (poly)peptide according to the third aspect from the viewpoint of adhesiveness to the norbornene-based polymer.

4) Immunoassay Method

The immunoassay method according to the fourth aspect is performed using a container having the inner surface that is composed of a norbornene-based polymer and the oligopeptide according to the second aspect is immobilized on.

Examples of the container to be used include a 96 well plate, a 384 well plate, and a cuvette. These containers can be molded by an injection molding method or the like. In addition, the container may be a well plate having a film of a norbornene-based polymer inserted on the bottom thereof or a channel chip manufactured by, for example, cutting a plate-like norbornene-based polymer.

Note that a portion of the surface of the above-mentioned container on which the above-mentioned oligopeptide is immobilized may be composed of at least the norbornene-based polymer described in detail above.

In addition, the surface on which the above-mentioned oligopeptide is immobilized may consist only of the norbornene-based polymer described in detail above, or the whole of the container may consist only of the norbornene-based polymer described in detail above.

In the method of immobilizing the above-mentioned oligopeptide on the inner surface of a container composed of a norbornene-based polymer, an aqueous solution containing the oligopeptide to be immobilized may be exposed to the inner surface of the container for a certain time. The aqueous solution may contain a buffer component such as a phosphate buffered saline, and may contain an organic solvent that dissolves in water such as dimethylsulfoxide.

The exposure operation to the container surface may be a method by adding an aqueous solution containing an oligopeptide to be immobilized into the container, a method by a dispenser such as an ink jet or a jet dispenser, a method by spraying, or a method by a stamp operation.

The temperature of the immobilization operation may be a room temperature. In the case of heating, the temperature may be within a temperature range in which the above-mentioned oligopeptide is not thermally denatured and it is possible to allow the water not to evaporate to cause a change in the solution concentration. In addition, the temperature may be in a cold storage state, and may be a temperature in which an aqueous solution containing an antigen to be immobilized does not freeze.

Thus, after contacting the above-mentioned oligopeptide, the solution is removed and washing with a phosphate buffered saline or the like is performed.

Although it is not necessary to carry out a special drying operation after the immobilizing operation, in order to remove a minute droplet remaining in the container after the immobilizing operation, a treatment such as air blowing or pressure reduction may be performed.

When the immobilized oligopeptide is an antigen or an antibody recognition site thereof (hereinafter collectively referred to as "antigen, etc."), a labeled antibody which binds to the antigen, etc. can be bound in the immunoassay.

The labeling substance for an antibody may be the same as a labeling substance used in a known immunoassay, and is not particularly limited. Examples of the labeling substance include enzymes, fluorescent substances, chemiluminescent substances, biotin, tags including His tag, nanoparticles including gold, hapten antigens, staining substances, isotopes, europium, and radioactive substances. As the enzyme, a known enzyme such as alkaline phosphatase (ALP), peroxidase, $\beta$-galactosidase, or the like may be employed, but the enzyme is not limited thereto.

In addition, in the immunoassay, after the above-mentioned oligopeptide is immobilized, a blocking treatment can be performed for the purpose of preventing non-specific adsorption of a (poly)peptide or the like on the inner surface of the container.

It is preferable to use a surfactant such as Tween® 20 (polyoxyethylene sorbitan monolaurate) for the blocking treatment. Alternatively, a protein such as albumin or milk casein may be used.

The immunoassay is carried out using the thus obtained container which has the inner surface that is composed of a norbornene-based polymer and an oligopeptide is immobilized on. The immunoassay utilizes an antigen-antibody reaction between an oligopeptide immobilized on the inner surface of a container composed of a norbornene-based polymer and an antibody in a solution. No specific limitations are placed on the measurement method in the immunoassay by combination with the container, and the measurement principle based on a generally known method such as a direct method, an indirect method, a sandwich method, or a competition method of ELISA can be applied.

Examples of the representative measurement method utilizing an antigen-antibody reaction between an oligopeptide immobilized on the inner surface of a container composed of a norbornene-based polymer and an antibody in a solution set forth above include (i) a method in which an antibody is previously bound to an oligopeptide immobilized in a container, followed by adding a sample containing a test substance, and (ii) a method in which the oligopeptide is immobilized, followed by adding a sample containing a test substance simultaneously with an antibody.

In method (i), an antibody modified with a label such as an enzyme, a fluorescent dye, or biotin, which specifically recognizes an oligopeptide is added into a container having the inner surface that is composed of a norbornene-based polymer and the oligopeptide is immobilized on, and allowed to react with the immobilized antigen, followed by washing and removing the unreacted excess antibody. Then, a sample to be measured is added into the container, and the antigen in the sample and the antibody in the container are allowed to react to recover the labeled antibody in the container. Thereafter, the antigen concentration in the sample is measured by measuring the labeling signal attributable to the recovered labeled antibody.

In method (ii), an antibody which is modified with a label such as an enzyme, a fluorescent dye, or biotin and specifically recognizes an antigen, and a sample containing a test substance is mixed, or simultaneously added independently without mixing in a container having the inner surface that is composed of a norbornene-based polymer and the oligopeptide is immobilized on, and allowed the antibody to react with the immobilized antigen, followed by recovering the labeled antibody that has not reacted with the immobilized antigen. Thereafter, the antigen concentration in the sample is measured by measuring the labeling signal attributable to the recovered labeled antibody.

In the above-mentioned methods (i) and (ii), although the sample to be measured is placed in the above-mentioned container during the measurement, a washing operation in the container after addition of the measurement sample is not required unlike in a generally known method such as a direct method, an indirect method, a sandwich method, or a competition method of ELISA.

In method (i), the antigen to be measured in the measurement sample is allowed to react with the labeled antibody previously adsorbed to the immobilized oligopeptide in the measurement container. Then the labeled antibody is eluted in the sample solution, the eluted antibody is removed, and the signal by the label is obtained, whereby the concentration of the measurement antigen in the measurement sample can be measured. Therefore, a washing operation in the container after addition of the measurement sample is not required.

In method (ii), the antigen to be measured in the measurement sample and the labeled antibody are simultaneously added into the measurement container. Although the labeled antibody in the measurement sample which has not react with the antigen to be measured reacts with the immobilized oligopeptide in the container, a signal that reflects the labeled antibody in the measurement sample that has reacted with the antigen to be measured can be measured by taking out the measurement sample and detecting the signal by the label of the labeled antibody contained in the sample. Therefore, a washing operation in the container after addition of the measurement sample is not required.

Thus, after the measurement sample is added into the container and allowed to immunologically react, only an operation for taking out the sample solution is required.

In a case in which the sample to be measured is a sample derived from a living body such as a human or a sample derived from a cultured cell, there is a risk of infection due to contamination of the sample with an infectious microorganism, and therefore attention should be paid at the time of handling the sample in order to prevent infection.

In an ELISA, in a case in which an antigen-antibody reaction is performed by placing a sample in a normal measurement container, washing the container is a general operation. In the washing operation, a large amount of the washing water is generated, and also in the operation of removing the washing solution from the container, mists or droplets of the washing solution are generated. Therefore, there are concerns that the washing water or the washing solution may be exposed to an operator or the inside of an automatic device. This increases the risk of infection if it cannot be denied that the sample may be contaminated with an infectious microorganism.

On the other hand, in the above-mentioned methods (i) and (ii), the risk of infection can be significantly reduced in the case of the measurement of a sample that has the undeniable possibility of being contaminated with an infectious microorganism, because the measurement can be performed without a washing operation after the sample to be measured is added to the measurement container. Therefore, the immunoassay can be safely and efficiently performed.

Note that the above-mentioned operations (i) and (ii) can be performed by a human manual operation, and may also be performed by a multi-channel automatic dispensing device, a robot, an arm type robot device, or the like.

In addition, in a measurement method that requires a washing operation, it takes time because the washing operation is repeated several times. On the other hand, in the above-mentioned methods (i) and (ii), more efficient measurement in a shorter time can be performed because a washing operation does not need to be performed.

EXAMPLES

The present disclosure will now be described in more detail by way of examples thereof. It should be noted, however, that the present disclosure is not limited at all by the following examples.

Example 1

<Acquisition of the Primary Phage Solutions>

As a phage display peptide library, Ph.D.-C7C Phage Display Peptide Library Kit (manufactured by New England Biolabs Japan Inc.) was used.

The phage solution was dissolved in a phosphate buffer (PBS; a mixed solution of 137 mmol/l NaCl, 8.1 mmol/l $Na_2HPO_4$, 2.68 mmol/l KCl, and 1.47 mmol/l $KH_2PO_4$, pH 7.4) to give a peptide library.

The prepared peptide library solution was added dropwise to the bottom of a culture dish that had a diameter of 10 cm and was made of a hydride of a norbornene-based ring-opened polymer [Zeonor® (Zeonor is a registered trademark in Japan, other countries, or both) 1060R, manufactured by Zeon Corporation], and allowed to stand at room temperature (25° C.) for 30 minutes.

Thereafter, the bottom of the culture dish was washed three times with PBS.

Subsequently, it was washed once with 40 mM Glycine.HCl Buffer (pH 2.2) adjusted to pH 2, and further, 40 mM Glycine.NaOH (pH 10) adjusted to pH 10 was added dropwise to it.

The dropped solution was collected, and the pH was immediately neutralized with a dilute hydrochloric acid (pH=7.0) to obtain a "phage solution washed with an alkali and collected".

Subsequently, a PBS containing 10% DMSO was added dropwise to the bottom of the culture dish, and the dropped solution was collected to obtain a "phage solution washed with DMSO and collected."

The flow chart of the process described so far is presented in FIG. 1.

<Acquisition of the Secondary Phage Solutions>

In order to promote the growth of the collected phage, a phage-infected *E. coli* was prepared by the following method.

Each of the phage solution washed with an alkali and collected, and the phage solution washed with DMSO and collected was added dropwise to an *E. coli* culture solution serving as a host of the phage, and cultured at 37° C. for 16 hours with shaking to obtain a phage-infected *E. coli* culture solution.

The phage solution washed with an alkali and collected, and the phage solution washed with DMSO and collected were obtained in the same manner as in the above-mentioned (Acquisition of the primary phage solutions) except that in place of the prepared peptide library solution, the phage-infected *E. coli* culture solution was added dropwise to the bottom of a culture dish that had a diameter of 10 cm and was made of a hydride of a norbornene-based ring-opened polymer [Zeonor® 1060R, manufactured by Zeon Corporation].

<Acquisition of the Tertiary Phage Solutions>

The above-mentioned two phage solutions thus obtained were used to infect *E. coli* in order to promote the growth of the phage again, and the phage solution washed with an alkali and collected, and the phage solution washed with DMSO and collected were obtained in the same manner as in acquisition of the secondary phage solutions.

<Genetic Analysis of the Phages>

The gene sequences of the phages contained in the two phage solutions obtained by acquisition of the tertiary phage solutions were read to obtain corresponding amino acid sequences.

The amino acid sequence obtained from the phage solution washed with an alkali and collected, i.e., the amino acid sequence having the property of eluting at a high pH, was TVDNSLA (Thr-Val-Asp-Asn-Ser-Leu-Ala) (SEQ ID NO: 2).

The amino acid sequence obtained from the phage solution washed with DMSO and collected, i.e., the amino acid sequence that continued to adhere even after washed with an alkali and was eluted with an organic solvent, was TVDSCLT (Thr-Val-Asp-Ser-Cys-Leu-Thr) (SEQ ID NO: 1).

Example 2

<Synthesis of Polypeptides>

A polypeptide having a histidine tag sequence in which 6 residues of histidine was arranged at the end for detection of the polypeptide, and glycine was linked between the amino acid sequence obtained in Example 1 and the histidine tag sequence was organically synthesized based on the amino acid sequence obtained in Example 1.

As Polypeptide 1 containing an amino acid sequence having the property of eluting at a high pH, AYTVDNSLACGGGGGHHHHHH (Ala-Tyr-Thr-Val-Asp-Asn-Ser-Leu-Ala-Cys-Gly-Gly-Gly-Gly-Gly-His-His-His-His-His-His) (SEQ ID NO: 3) was synthesized.

As Polypeptide 2 containing an amino acid sequence having the property of eluting with DMSO, ACTVDSCLTCGGGGGHHHHHH (Ala-Cys-Thr-Val-Asp-Ser-Cys-Leu-Thr-Cys-Gly-Gly-Gly-Gly-Gly-His-His-His-His-His-His) (SEQ ID NO: 4) was synthesized.

<Preparation of Polypeptide Solutions>

Polypeptide 1, Polypeptide 2, and a human normal IgG antibody (manufactured by Wako Pure Chemical Industries, Ltd.) were dissolved in a PBS solution and 10% DMSO in PBS (10% DMSO PBS) each in a concentration of 10 μg/ml to give various solutions.

<Evaluation of Adhesiveness to the Container>

To a 96-well plate obtained by injection molding of a hydride of a norbornene-based ring-opened polymer [Zeonor® 1060R, manufactured by Zeon Corporation] (hereinafter referred to as a "1060R plate") and a 96-well plate made of polystyrene (product name "Falcon® (Falcon is a registered trademark in Japan, other countries, or both)", manufactured by Corning Incorporated; hereinafter referred to as a "TCPS plate"), each of the polypeptide solutions prepared above was added in an amount of 50 μL/well (N=3) and the plates were allowed to stand at room temperature (25° C.) for 1 hour.

After allowed to stand, the insides of the wells of the 1060R plate and the TCPS plate were washed three times with T-TBS (0.05 m Tris hydrochloric acid, 0.15 m sodium chloride, 0.05% Tween® 20; pH 7.6). After that, a blocking operation was performed by dispensing 200 μL per well of a 5-fold diluted solution of Blocking One reagent manufactured by NACALAI TESQUE, INC. as a blocking solution and allowing the plates to stand for 1 hour at room temperature.

Each plate after allowed to stand was washed 5 times with T-TBS. After washing, 50 μL per well of a PBS solution of (a mouse anti-6-His monoclonal antibody, manufactured by NACALAI TESQUE, INC.) was added to each plate and the plates were allowed to stand at room temperature for 1 hour for detection of the polypeptide.

Furthermore, each plate after allowed to stand was washed 5 times with T-TBS (the same as above). After washing, 50 μL per well of a peroxidase coloring reagent was added, and allowed to occur a coloring reaction for 10 minutes at room temperature, followed by adding 100 μL of 100 mM aqueous hydrochloric acid solution to stop the peroxidase reaction.

For the wells of each plate, the absorbance at 450 nm was measured using a well plate reader apparatus (manufactured by CORONA ELECTRIC Co., Ltd.).

Figure 2:
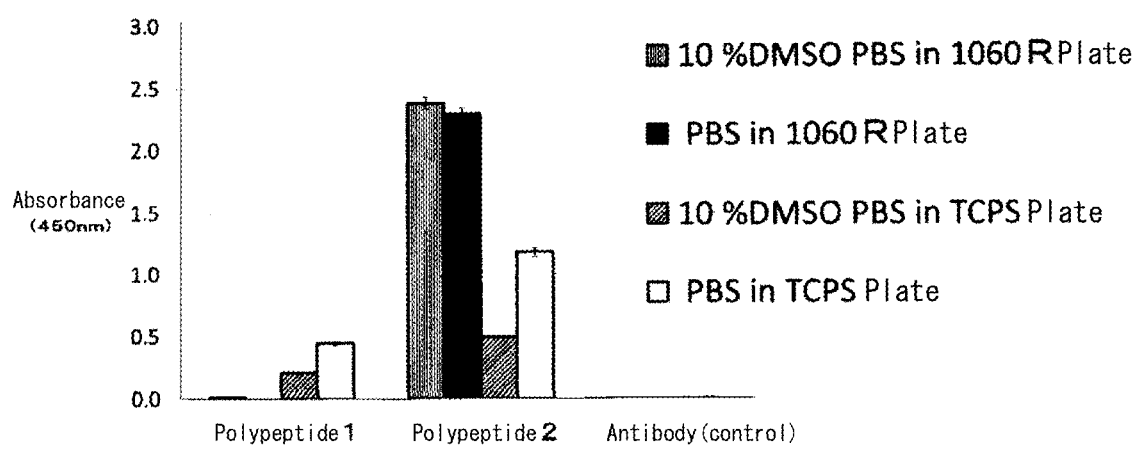
FIG. 2 is a graph indicating the evaluation results of adhesiveness of oligopeptides obtained in Example 2 to various polymer products.

The measurement results are presented in FIG. 2. FIG. 2 presents the result of each of different combinations of solvents in which polypeptides were dissolved and plates for each polypeptide.

For Polypeptide 2, the result indicates that the absorbance at 450 nm of the 1060R plate was higher than that of the TCPS plate. Therefore, it was indicated that the oligopeptide having the amino acid sequence contained in Polypeptide 2 has high adhesiveness to a norbornene-based polymer.

Example 3

A norbornene-based polymer adhesive-modified (poly)peptide "ACTVDSCLTCGGGGGRGDSPHHHHHH (Ala-Cys-Thr-Val-Asp-Ser-Cys-Leu-Thr-Cys-Gly-Gly-Gly-Gly-Gly-Arg-Gly-Asp-Ser-Pro-His-His-His-His-His-His)" (Polypeptide 3) (SEQ ID NO: 5) was synthesized in which a RGD motif, RGDSP (Arg-Gly-Asp-Ser-Pro) was inserted in front of the histidine tag of Example 2 in order to add a recognition amino acid sequence RGD (Arg-Gly-Asp) of integrin which is a receptor of fibronectin or the like on the cell surface to Polypeptide 2 having an amino acid that has high adhesiveness to a norbornene-based polymer in Example 2.

Each of the solutions which this Polypeptide 3 and Polypeptide 2 obtained in Example 2 were dissolved in PBS in a concentration of 10 μg/ml respectively was filter-sterilized. To an EOG-sterilized 1060R plate, 50 μL per well of each of the resultant solution was added. The plates were allowed to stand at room temperature (25° C.) for 1 hour.

After allowed to stand, each of the 1060R plates incubated with Polypeptide 3 and Polypeptide 2 obtained in Example 2 was washed three times with sterilized PBS to obtain a Polypeptide 3-coated 1060R plate and a Polypeptide 2-coated 1060R plate.

To wells of the two plates thus obtained and a 1060R plate that was not coated with a polypeptide, CHO (Chinese Hamster Ovary) cells suspended in a serum-free medium (serum free medium ESF SFM Serum • Free Medium for Hybridoma, CHO & 293 Cells, manufactured by Expression Systems, LLC) were added and maintained the culture in a CO 2 incubator at 37° C.

When the cells were observed with a microscope 5 hours after the start of culture, CHO cells in the wells of the Polypeptide 3-coated 1060R plate had the effect of the RGD sequence and exhibited shapes in which the cells were stretched.

Figure 3:
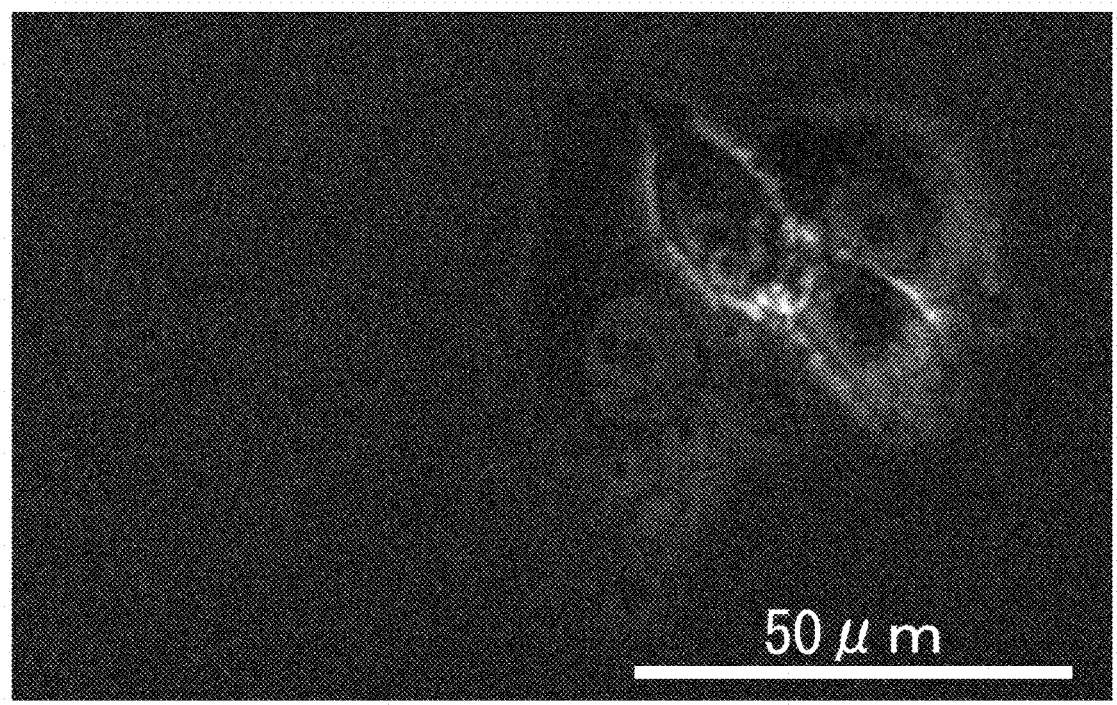
FIG. 3 is a photomicrograph of CHO cells on a 1060 R dish to which Polypeptide 3 is adhered in Example 3.

A photomicrograph of the CHO cells on the 1060R plate to which Polypeptide 3 is adhered is presented in FIG. 3.

Figure 4:
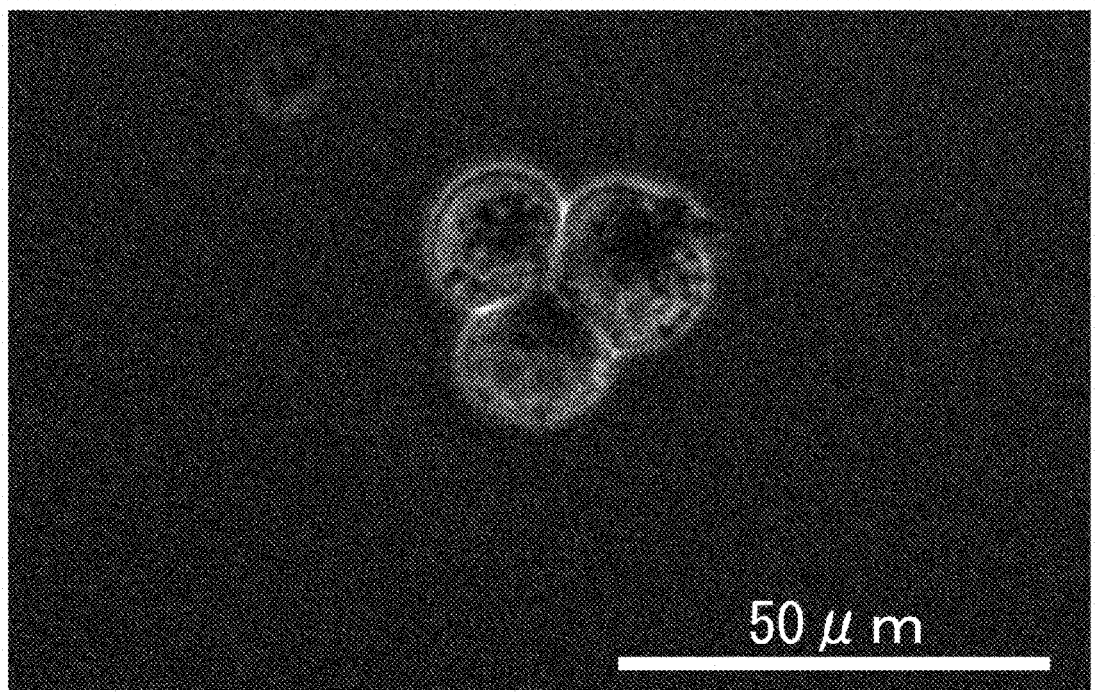
FIG. 4 is a photomicrograph of CHO cells on a 1060 R dish to which Polypeptide 2 is adhered in Example 3.

However, as observed in FIG. 4, the cells had rounded shapes since in the wells of the Polypeptide 2-coated 1060R plate without the RGD sequence, the RGD sequence was not placed on the surface of the 1060R plate.

Figure 5:
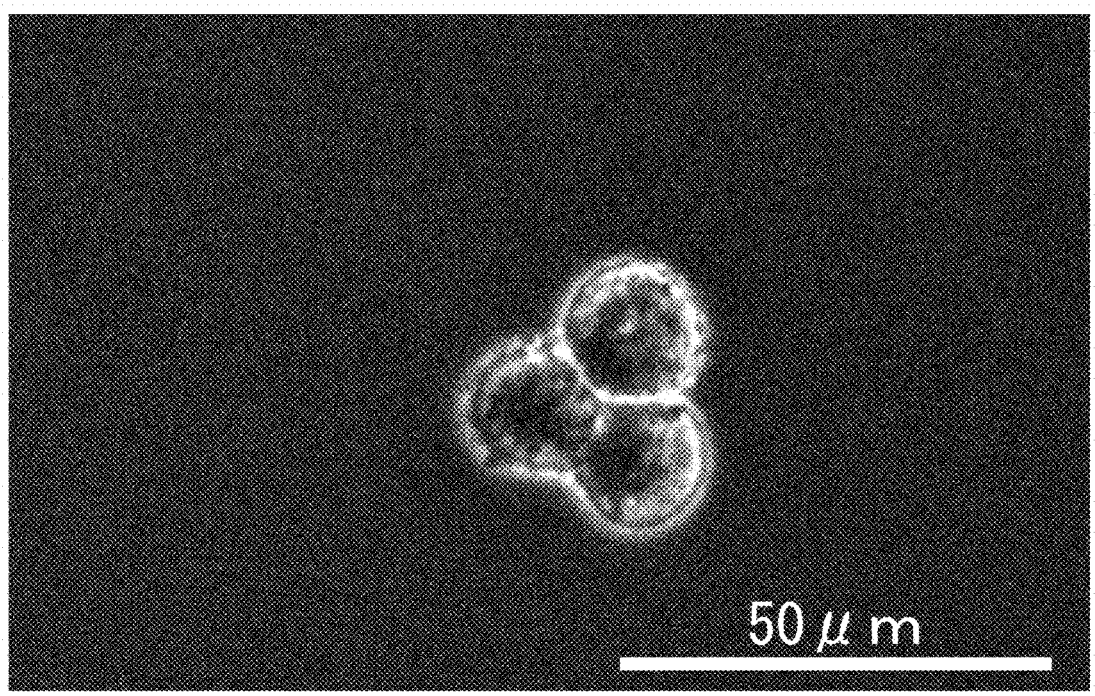
FIG. 5 is a photomicrograph of CHO cells on a 1060 R dish to which neither Polypeptide 2 nor 3 is adhered in Example 3.

In addition, the CHO cells also had rounded shapes in the 1060R plate that was not coated with a polypeptide. As observed in FIG. 5, the cells did not exhibit stretched shapes.

From these results, it was indicated that the oligopeptide according to one of the aspects is combined with another peptide such as an RGD sequence that controls cell adhesion to allow for coating of a polypeptide containing the oligopeptide on the surface of a norbornene-based polymer and controlling a state of adhesiveness or the like of a cell on a COP surface.

In the following Examples, BNP (brain natriuretic peptide) was used as the substance to be measured by way of illustration, but the substance to be measured is not limited thereto.

Example 4

The condition for adsorption of an antigen to a multi-well plate was examined. A comparison of adsorption of an antigen was made by using a 96-well plate obtained by injection molding of a hydride of a norbornene-based ring-opened polymer [Zeonor® 1060R, manufactured by Zeon Corporation] (hereinafter referred to as a "1060R plate") and a 96-well plate made of polystyrene (product name "SUMILON® (SUMILON is a registered trademark in Japan, other countries, or both) ELISA Plate H", manufactured by Sumitomo Bakelite Co., Ltd.; hereinafter referred to as a "PS plate").

A peptide in which the amino acid sequence of Ala-Cys-Thr-Val-Asp-Ser-Cys-Leu-Thr-Cys-Gly-Gly-Gly-Gly-Gly-Ser-Ser-Ser-Gly-Leu-Gly (SEQ ID NO: 7) that has the property of specifically attaching to a norbornene-based polymer is bound to the N terminal of the amino acid sequence of Cys-Lys-Val-Leu-Arg-Arg-His (SEQ ID NO: 6) of the antibody recognition site of the human BNP (brain natriuretic peptide) (hereinafter referred to as a "synthetic BNP antigen") was synthesized. The synthetic BNP antigen was dissolved in a phosphate buffered saline (NaCl 8.0 g/L, KCl 0.20 g/L, Na$_2$HPO$_4$ 1.44 g/L, KH$_2$PO$_4$ 0.24 g/L; pH 7.4; the same shall apply hereinafter) so as to obtain diluted samples having concentrations of 1×10$^7$ pg/µL, 53 pg/µL, and 27 pg/µL. To three wells, 100 µL of each diluted material was added, and the resultant was allowed to stand at room temperature for 30 minutes, and washed three times with a phosphate buffered saline containing 0.05% Tween® 20. Then, 200 µL of a blocking agent diluted 10-fold with a phosphate buffered saline (manufactured by NACALAI TESQUE, INC., product name "Blocking One") was dispensed into each well, and the resultant was allowed to stand at room temperature for 30 minutes, and washed three times with a phosphate buffered saline containing 0.05% Tween® 20 to immobilize the synthetic BNP antigen on the plate.

Subsequently, 100 µL of a phosphate buffered saline containing 0.25 ng/µL of a horseradish peroxidase-labeled antibody was added to each well, and the resultant was allowed to stand at room temperature for 30 minutes, and washed three times with a phosphate buffered saline containing 0.05% Tween® 20.

Then, the synthetic BNP antigen immobilized in the plate was allowed to develop a color using a coloring reagent (manufactured by NACALAI TESQUE, INC., product name "ELISA POD Substrate TMB Solution"), and quenched with a dilute sulfuric acid, followed by measuring the absorbance at 450 nm by an absorbance plate reader.

Figure 6:
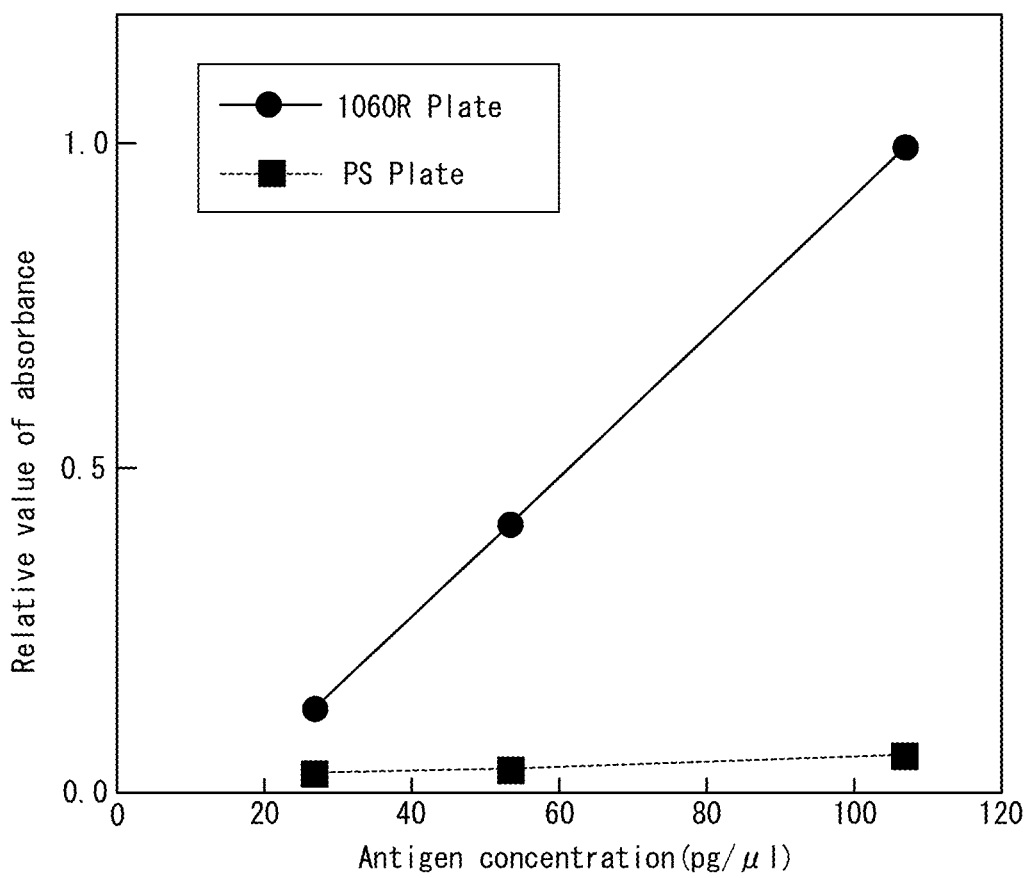
FIG. 6 is a graph indicating the relationship between antigen concentration and absorbance.

As a result, as observed in FIG. 6, it was confirmed that although the synthetic BNP antigen was not attached to the PS plate, the synthetic BNP antigen was attached to the 1060R plate.

Example 5

<Preparation of the Plate for the Measurement of BNP>

The synthetic BNP antigen synthesized in Example 1 was immobilized on the 1060R plate in the same manner as in Example 4 except that an antigen solution was prepared by dissolving the synthetic BNP antigen in a phosphate buffered saline so as to have a concentration of 98 pg/µL, and 100 µL of the antigen solution was dispensed to each well (7 wells) of the plate.

Subsequently, 50 µL of a phosphate buffered saline containing 0.25 ng/µL of a horseradish peroxidase-labeled antibody diluted with a phosphate buffered saline was added to each well, and the resultant was allowed to stand at room temperature for 30 minutes, and washed three times with a phosphate buffered saline containing 0.05% Tween® 20 to obtain the plate for the measurement of BNP.

<BNP Measurement>

The diluted samples (7 samples) were prepared by dissolving human BNPs (manufactured by PEPTIDE INSTITUTE, INC.) in a phosphate buffered saline so as to have concentrations of 2.0 pg/ml, 3.9 pg/ml, 7.8 pg/ml, 15.6 pg/ml, 31.3 pg/ml, 62.5 pg/ml, and 125 pg/ml. To each well of the obtained plate for the measurement of BNP, 100 µL of the diluted sample was added, and the resultant was allowed to stand at room temperature for 30 minutes, followed by recovering 50 µL of the solution in a well and transferring the recovered solution to another multi-well plate.

The transferred solution was allowed to develop a color using a coloring reagent (manufactured by NACALAI TESQUE, INC., product name "ELISA POD Substrate TMB Solution"), and quenched with a dilute sulfuric acid, followed by measuring the absorbance at 450 nm by an absorbance plate reader.

Figure 7:
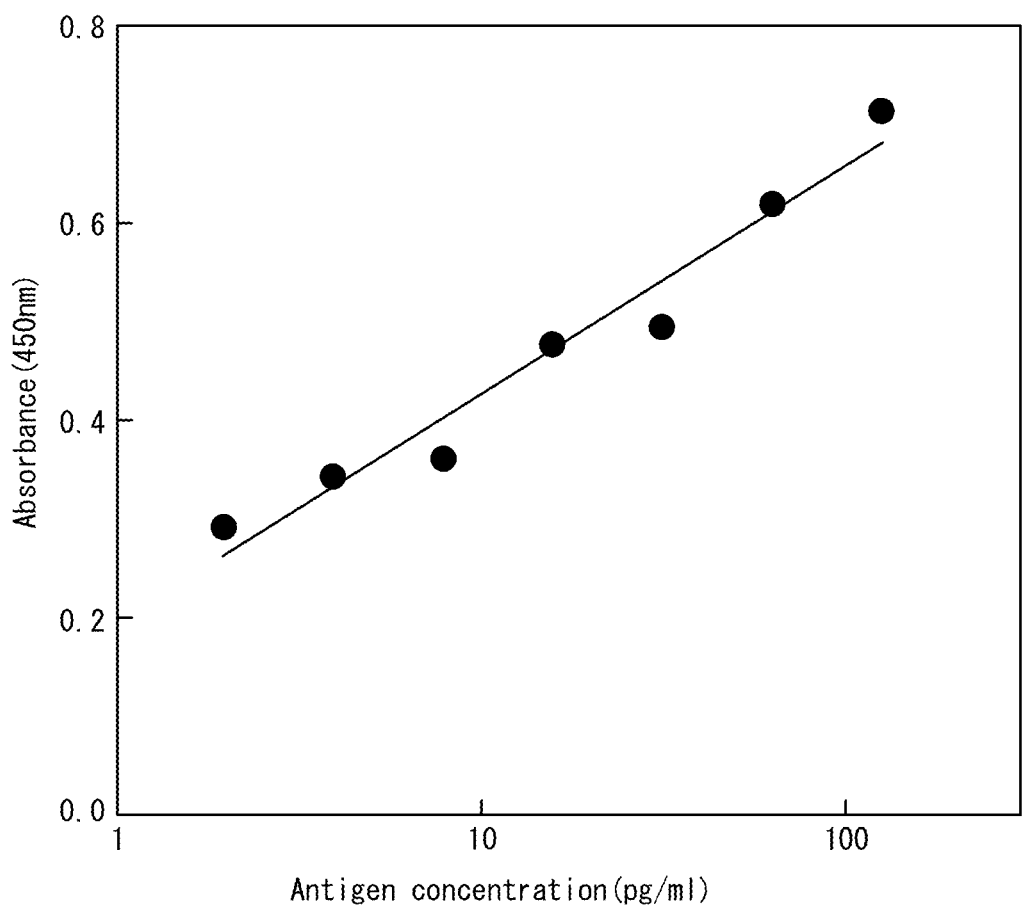
FIG. 7 is a graph indicating the relationship between antigen concentration and absorbance.

As a result, as observed in FIG. 7, it was indicated that color development was observed depending on the BNP concentration used, and the BNP concentration can be calculated by measuring the absorbance.

Example 6

A comparison was made between the effect of a method using a protein widely used in ELISA for a blocking operation of the surface of a norbornene-based polymer and the effect of a method using Tween® 20 for the operation.

The container on which the synthetic BNP antigen was immobilized was blocked in the same manner as in Example 5, using a phosphate buffered saline containing 10% blocking agent (manufactured by NACALAI TESQUE, INC., product name "Blocking One") containing a widely used casein ("Blocking One having a final concentration of 10%"), a phosphate buffered saline containing 0.05% Tween® 20 ("Tween® 20 PBS having a final concentration of 0.05%"), and a phosphate buffered saline containing 0.2% Tween® 20 ("Tween® 20 PBS having a final concentration of 0.2%") as blocking agents, and compared to the condition without the blocking treatment.

As microwell plates, the 1060R plate (experimental example) and the PS plate (comparative example) were used.

In the blocking treatment, 200 µL of the blocking agent was added to each well (3 wells), and the resultant was allowed to stand at room temperature for 20 minutes, and washed three times with a phosphate buffered saline containing 0.05% Tween® 20. Then, an antibody solution dissolved in a phosphate buffered saline in which 0.25 ng/4 of a horseradish peroxidase-labeled antibody was contained was prepared, 50 µL of the antibody solution was added to a well of the 96 well plate, and the resultant was allowed to stand at room temperature for 60 minutes.

After the resultant was allowed to stand, the solution in the wells was removed, followed by washing three times with a phosphate buffered saline containing 0.05% Tween® 20. Subsequently, 50 µL of a coloring reagent (manufactured by NACALAI TESQUE, INC., product name "ELISA POD Substrate TMB Solution") was added to a well of the 96 well plate, and the plate was allowed to stand at room temperature for 5 minutes. After adding 0.1 M sulfuric acid as a stop solution, the absorbance at 450 nm was measured with a light absorption plate reader.

The combinations of the experimental conditions are described in Table 1.

TABLE 1

| Experimental condition | Plate | Blocking treatment |
| --- | --- | --- |
| Experiment 3-1 | 1060R Plate | Blocking One PBS having a final concentration of 10% |
| Experiment 3-2 | 1060R Plate | Tween ® 20 PBS having a final concentration of 0.05% |
| Experiment 3-3 | 1060R Plate | Tween ® 20 PBS having a final concentration of 0.2% |
| Experiment 3-4 | 1060R Plate | None |
| Comparative Experiment 3-1 | PS Plate | Blocking One PBS having a final concentration of 10% |
| Comparative Experiment 3-2 | PS Plate | Tween ® 20 PBS having a final concentration of 0.05% |
| Comparative Experiment 3-3 | PS Plate | Tween ® 20 PBS having a final concentration of 0.2% |
| Comparative Experiment 3-4 | PS Plate | None |

The value for each condition was determined using the relative value to the measured absorbance value of the well that was not subjected to blocking in the 1060R plate.

Figure 8:
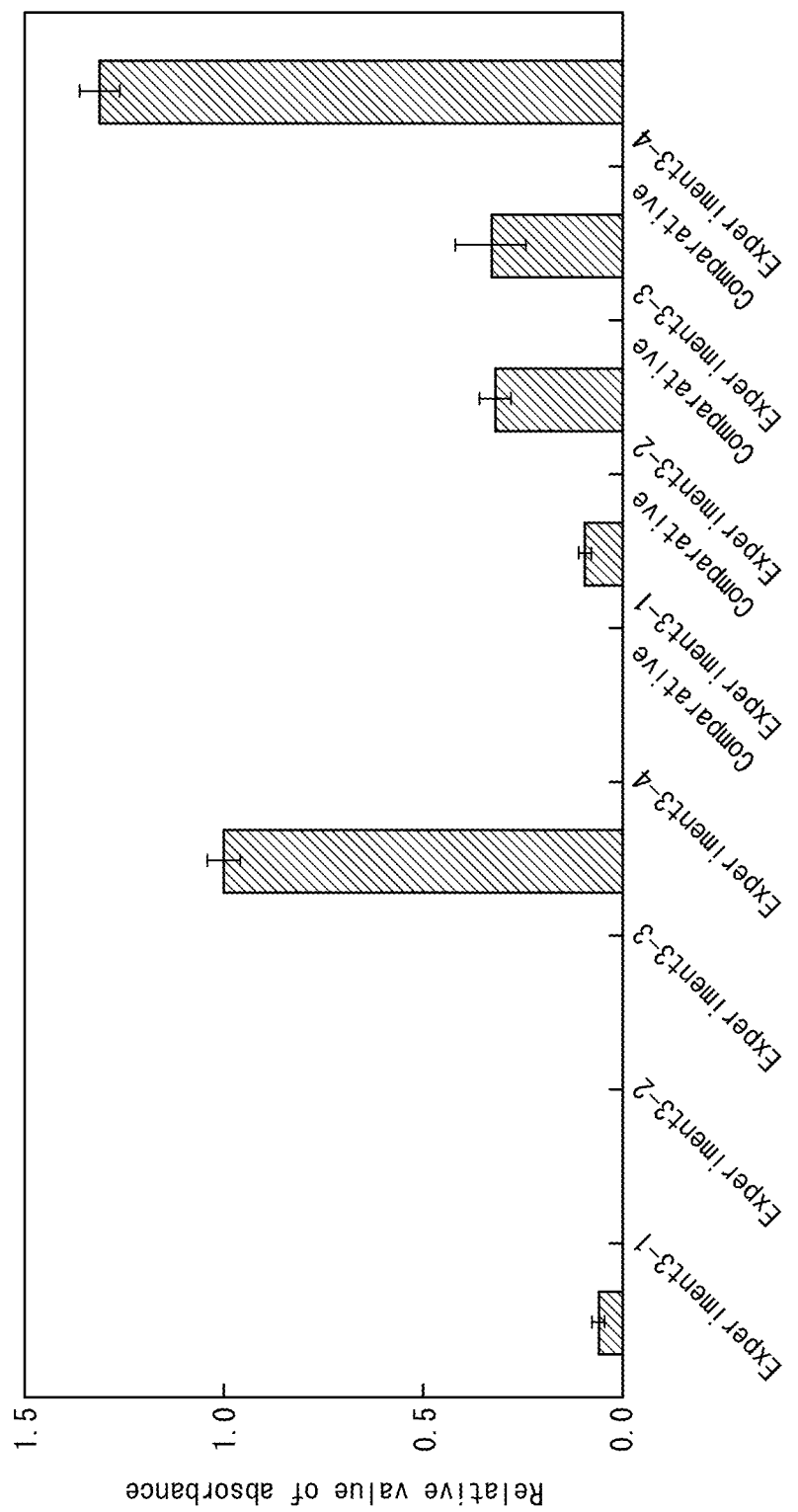
FIG. 8 is a graph indicating the influence of a blocking agent on absorbance.

As a result, as observed in FIG. 8, for the 1060R plate, a blocking effect was observed with a solution containing no protein and containing Tween® 20, indicating that a non-specific adsorption of an antibody was suppressed. For the PS plate, in the case of containing no protein, although the adsorption was less as compared to the untreated case, a blocking effect was lower as compared to a blocking agent containing a protein.

Example 7

The example of a method in which an immobilized antigen is immobilized in a container, and an antibody is added simultaneously with a sample will be described.

<Preparation of the Plate for the Measurement of BNP>

A blocking treatment was performed by preparing an antigen solution having a concentration of 122 pg/4 with the synthetic BNP antigen obtained in Example 4 and a phosphate buffered saline, dispensing 75 µL of the antigen solution to each well of the 1060R plate, allowing the plate to stand at room temperature for 1 hour, washing twice with a phosphate buffered saline containing 0.05% Tween® 20, and allowing the plate to stand at room temperature for 10 minutes with a phosphate buffered saline containing 0.05% Tween® 20.

<BNP Measurement>

The diluted samples of human BNPs (manufactured by PEPTIDE INSTITUTE, INC.) were prepared so as to have concentrations of 18 pg/µL, 4 pg/µL, and 1 pg/µL. Then 504 of these diluted samples and 50 µL of a solution in which a horseradish peroxidase-labeled antibody capable of recognizing a human BNP was diluted with a phosphate buffered saline were mixed, and 100 µL of the resultant solution was added to each well (3 wells) of the above-described plate for the measurement of BNP. The resultant was allowed to stand at room temperature for 30 minutes.

Subsequently, 50 µL of the solution in the well was taken out, and a coloring reagent (manufactured by NACALAI TESQUE, INC., product name "ELISA POD Substrate TMB Solution") was added to measure the absorbance.

Figure 9:
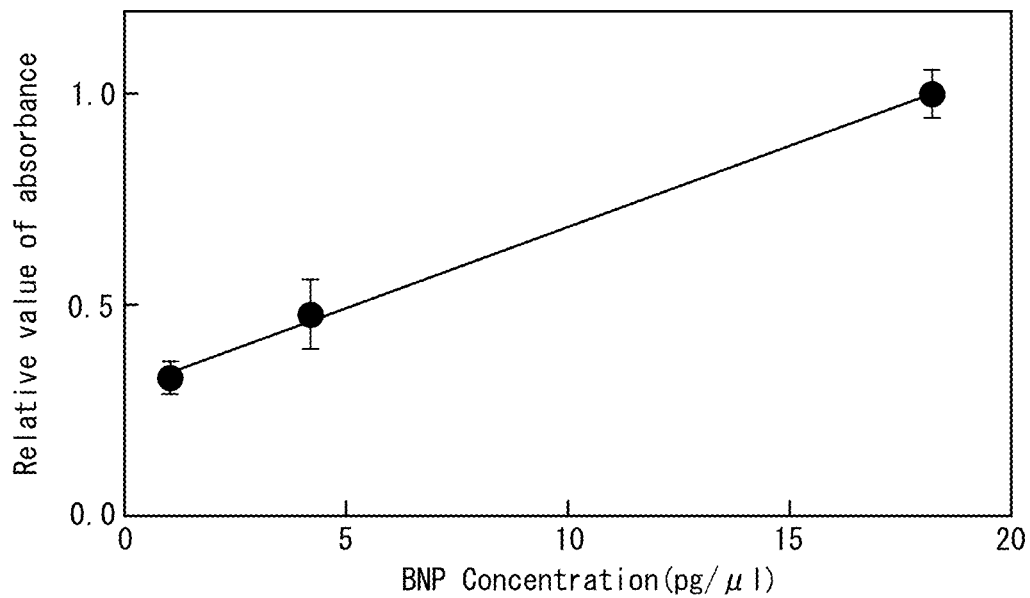
FIG. 9 is a graph indicating the relationship between BNP concentration and absorbance.

As a result, as observed in FIG. 9, light absorption was observed in a BNP concentration dependent manner, and it was indicated that an immunoassay can be performed by a method in which a plate on which an antigen is immobilized is prepared in a container made of a norbornene-based polymer, and an antibody is added simultaneously with a sample.

The invention claimed is:

1. An oligopeptide consisting of the amino acid sequence of Thr-Val-Asp-Ser-Cys-Leu-Thr (SEQ ID NO: 1).

2. The oligopeptide according to claim 1, wherein the oligopeptide has adhesiveness to a norbornene-based polymer.

3. The oligopeptide according to claim 2, wherein the norbornene-based polymer is a hydrogenated ring-opened polymer of a norbornene-based monomer.

* * * * *